United States Patent
Burnett

(10) Patent No.: US 8,865,063 B2
(45) Date of Patent: Oct. 21, 2014

(54) METHOD AND APPARATUS FOR AUTOMATED ACTIVE STERILIZATION OF FULLY IMPLANTED DEVICES

(75) Inventor: Daniel Rogers Burnett, San Francisco, CA (US)

(73) Assignee: TheraNova, LLC, San Francisco, CA (US)

( * ) Notice: Subject to any disclaimer, the term of this patent is extended or adjusted under 35 U.S.C. 154(b) by 0 days.

(21) Appl. No.: 12/702,977

(22) Filed: Feb. 9, 2010

(65) Prior Publication Data
US 2010/0256607 A1    Oct. 7, 2010

Related U.S. Application Data

(63) Continuation of application No. PCT/US2008/073279, filed on Aug. 15, 2008.

(60) Provisional application No. 60/964,822, filed on Aug. 15, 2007.

(51) Int. Cl.
| | |
|---|---|
| *A61L 2/00* | (2006.01) |
| *A61L 2/10* | (2006.01) |
| *A61L 2/18* | (2006.01) |
| *A61L 2/025* | (2006.01) |
| *A61L 2/12* | (2006.01) |
| *A61L 2/08* | (2006.01) |
| *A61F 2/82* | (2013.01) |
| *A61F 2/04* | (2013.01) |

(52) U.S. Cl.
CPC . *A61L 2/025* (2013.01); *A61L 2/10* (2013.01); *A61F 2/82* (2013.01); *A61L 2/18* (2013.01); *A61F 2/042* (2013.01); *A61L 2/12* (2013.01); *A61L 2/08* (2013.01)
USPC .......................................................... 422/20

(58) Field of Classification Search
CPC ............................ A61L 2202/24; A61L 2/025
USPC .......................................................... 422/20
See application file for complete search history.

(56) References Cited

U.S. PATENT DOCUMENTS

| 4,271,827 A | 6/1981 | Angelchik |
| 4,702,232 A | 10/1987 | Gardner et al. |

(Continued)

FOREIGN PATENT DOCUMENTS

| WO | WO 03/082363 | 10/2003 |
| WO | WO 2009/023818 | 2/2009 |

*Primary Examiner* — Kevin Joyner
(74) *Attorney, Agent, or Firm* — Levine Bagade Han LLP

(57) ABSTRACT

The current invention provides this advance in infection control via its unique application of active sterilization to a catheter or implant. While most catheters, and many implants, are passive devices, the current invention will provide an active component as a integral part of the implanted catheter or device to continuously or intermittently sterilize the exposed surfaces/areas of the device. This active sterilization may be accomplished by a variety of mechanisms, including, application of heat, RF, microwave, ultrasound, ultraviolet radiation or other energy capable of sterilizing the device or dislodging any problematic Biofilm that may form. The active sterilization may also employ the pumping of a sterilizing chemical from an attached drug reservoir, the use of electricity or freezing temperatures or any other mechanism for either inhibiting, killing or dislodging any infectious material in contact with the implant. One major advantage of this design is that through the use of a small, battery powered or inductively powered sterilization element, the implanted catheter or device can be effectively sterilized without requiring the standard removal surgery, waiting period, then replacement of the infected device. This is expected to translate into greatly improved outcomes (particularly for devices where infection may be catastrophic, ie a prosthetic knee or hip), greatly improved costs, and greatly improved longevity of susceptible devices (ie IV ports, etc.).

13 Claims, 2 Drawing Sheets

(56) References Cited

U.S. PATENT DOCUMENTS

| | | | |
|---|---|---|---|
| 4,841,956 A | 6/1989 | Gardner et al. | |
| 5,240,675 A * | 8/1993 | Wilk et al. | 422/22 |
| 5,260,020 A * | 11/1993 | Wilk et al. | 422/22 |
| 5,263,473 A | 11/1993 | McWhorter | |
| 5,295,958 A | 3/1994 | Shturman | |
| 5,411,552 A | 5/1995 | Andersen et al. | |
| 5,514,079 A | 5/1996 | Dillon | |
| 5,549,709 A | 8/1996 | Caspers | |
| 5,725,593 A | 3/1998 | Caracciolo | |
| 5,840,081 A | 11/1998 | Andersen et al. | |
| 5,865,729 A | 2/1999 | Meehan et al. | |
| 5,897,518 A | 4/1999 | Shaw | |
| 6,053,940 A | 4/2000 | Wijay | |
| 6,080,163 A | 6/2000 | Hussein et al. | |
| 6,186,614 B1 | 2/2001 | Nagashima | |
| 6,206,831 B1 * | 3/2001 | Suorsa et al. | 600/439 |
| 6,264,700 B1 | 7/2001 | Kilcoyne et al. | |
| 6,334,873 B1 | 1/2002 | Lane et al. | |
| 6,350,281 B1 | 2/2002 | Rhee | |
| 6,551,280 B1 | 4/2003 | Knighton et al. | |
| 6,589,194 B1 | 7/2003 | Calderon et al. | |
| 6,648,842 B2 | 11/2003 | Horkel | |
| 6,726,726 B2 | 4/2004 | Caspers | |
| 6,875,231 B2 | 4/2005 | Anduiza et al. | |
| 7,175,652 B2 | 2/2007 | Cook et al. | |
| 7,850,704 B2 | 12/2010 | Burnett et al. | |
| 2002/0055731 A1 * | 5/2002 | Atala et al. | 604/522 |
| 2002/0128719 A1 | 9/2002 | Burkinshaw | |
| 2003/0191356 A1 | 10/2003 | Moreci | |
| 2005/0197563 A1 * | 9/2005 | Helfer et al. | 600/410 |
| 2006/0069400 A1 | 3/2006 | Burnett et al. | |
| 2006/0116695 A1 | 6/2006 | Poutiasrine | |
| 2006/0282175 A1 | 12/2006 | Haines et al. | |
| 2009/0030435 A1 | 1/2009 | Burnett et al. | |

* cited by examiner

METHOD AND APPARATUS FOR AUTOMATED ACTIVE STERILIZATION OF FULLY IMPLANTED DEVICES

CROSS-REFERENCE TO RELATED APPLICATIONS

This application is a continuation of International Pat. App. Ser. No. PCT/US2008/073279 filed Aug. 15, 2008 which claims the benefit of priority to U.S. Prov. Pat. App. 60/964,822 filed Aug. 15, 2007, each of which is incorporated herein by reference in its entirety.

FIELD OF THE INVENTION

The present invention relates to the field of medical devices, in particular catheters and other implantable devices in the body that are susceptible to infection.

BACKGROUND OF THE INVENTION

In the last few decades, there has been incredible progress in a variety of medical fields. At the same time, though, many fields have stymied and remained stagnant. Once such field is the treatment and prevention of catheter and implant infections. Despite many of the issues associated with indwelling catheters and implants, the primary of which is infection in many cases, there has been little effort put forth to solve these problems and the medical community at large just accepts these complications as a fact of life. What effort has been put forth to combat this problem has been directed at the sterilization of externalized catheters and devices. These devices typically are highly prone to infection, but they can be sterilized through the external application of anti-infective measures. The prior art in this field, then, mostly consists of devices and methods for sterilizing indwelling catheters and devices through the external application of bactericidal measures.

Fully implantable devices for the prevention of infection, though, have been limited to bactericidal and bacteriostatic coatings or the application of a small current/voltage to prevent bacterial adhesion. The use of an electronegative field to prevent bacterial adhesion, though, has been in development for quite some time and there is still no device that has been successfully commercialized with this feature due to the energy demands and poor cost-efficacy. The present innovation, then, provides a fully implantable novel device and method capable of actively preventing and treating infection of an indwelling catheter or implant.

SUMMARY OF THE INVENTION

The current invention provides this advance in infection control via its unique application of active sterilization to a catheter or implant. While most catheters, and many implants, are passive devices, the current invention will provide an active component as a integral part of the implanted catheter or device to continuously or intermittently sterilize the exposed surfaces/areas of the device. This active sterilization may be accomplished by a variety of mechanisms, including, application of heat, RF, microwave, ultrasound, ultraviolet radiation or other energy capable of sterilizing the device or dislodging any problematic biofilm that may form. The active sterilization may also employ the pumping of a sterilizing chemical from an attached drug reservoir, the use of electricity or freezing temperatures or any other mechanism for either inhibiting, killing or dislodging any infectious material in contact with the implant. One major advantage of this design is that through the use of a small, battery powered or inductively powered sterilization element, the implanted catheter or device can be effectively sterilized without requiring the standard removal surgery, waiting period, then replacement of the infected device. This is expected to translate into greatly improved outcomes (particularly for devices where infection may be catastrophic, ie a prosthetic knee or hip), greatly improved costs, and greatly improved longevity of susceptible devices (ie IV ports, etc.).

In its preferred catheter (or any device with no moving parts) embodiment, an ultrasonic energy generator (including batter, circuit board, etc.) may incorporated into the base of an intravascular injection port and the port and catheter may be intermittently subjected to a vigorous ultrasonic wave to break free any potential biofilm that may have formed in the interim. This wave may, preferably, be powered by an internal battery and run on a programmed schedule. The device may also alert the user or healthcare practitioner that the battery charge is low by simple vibration or other communication mechanisms. Other sources of energy may be utilized, as well, including ultraviolet radiation, temperature extremes (ie freezing/heating), EMF, RF, microwave (or other energy source) and/or actively pumped drug. In its ideal and most practical embodiments, the internally powered sterilization device may also be transcutaneously activated and/or recharged (ie inductive recharging through the use of an external coil providing pulsed magnetic fields) so that it need not be removed simply due to battery depletion. This is a critical feature for devices with long-term implantation and not as essential for devices with short-term residence. As long-term implants are the most susceptible to infection; though, these are also the devices that will need this protection the most, so in its preferred embodiment the device will incorporate an inductive recharging element. The device may also be capable of communicating to the user the status of the device and/or usage statistics for the device i.e. number of times the port has been accessed, pressure inside the port (an indication of clogging, etc.)

In its preferred fluid pumping embodiment, the device of the present invention may entail one or more sterilization features. In its ideal embodiment, the device of the present invention provides for an in-line sterilization element capable of sterilizing fluid that passes through its conduits to prevent spread of infection. This may entail ultrasonic energy, mechanical energy (i.e. a rapidly spinning wire), ultraviolet radiation, temperature extremes (ie freezing or heating by liquid nitrogen, Peltier junction, or other means), EMF, RF, microwave (or other energy source) and/or actively pumped drug. The outside of the conduit may also be sterilized continuously or intermittently via one or more of these mechanisms. In its ideal embodiment, the tubing of the fluid pump may be exposed to an ultraviolet LED that has low current draw but which is capable of sterilizing stagnant fluid or low volume flow. This design is optimal when used to prevent retrograde spread of infection (ie when a pump is parked or is in line with a backcheck valve).

DETAILED DESCRIPTION OF THE INVENTION

Figure 1:
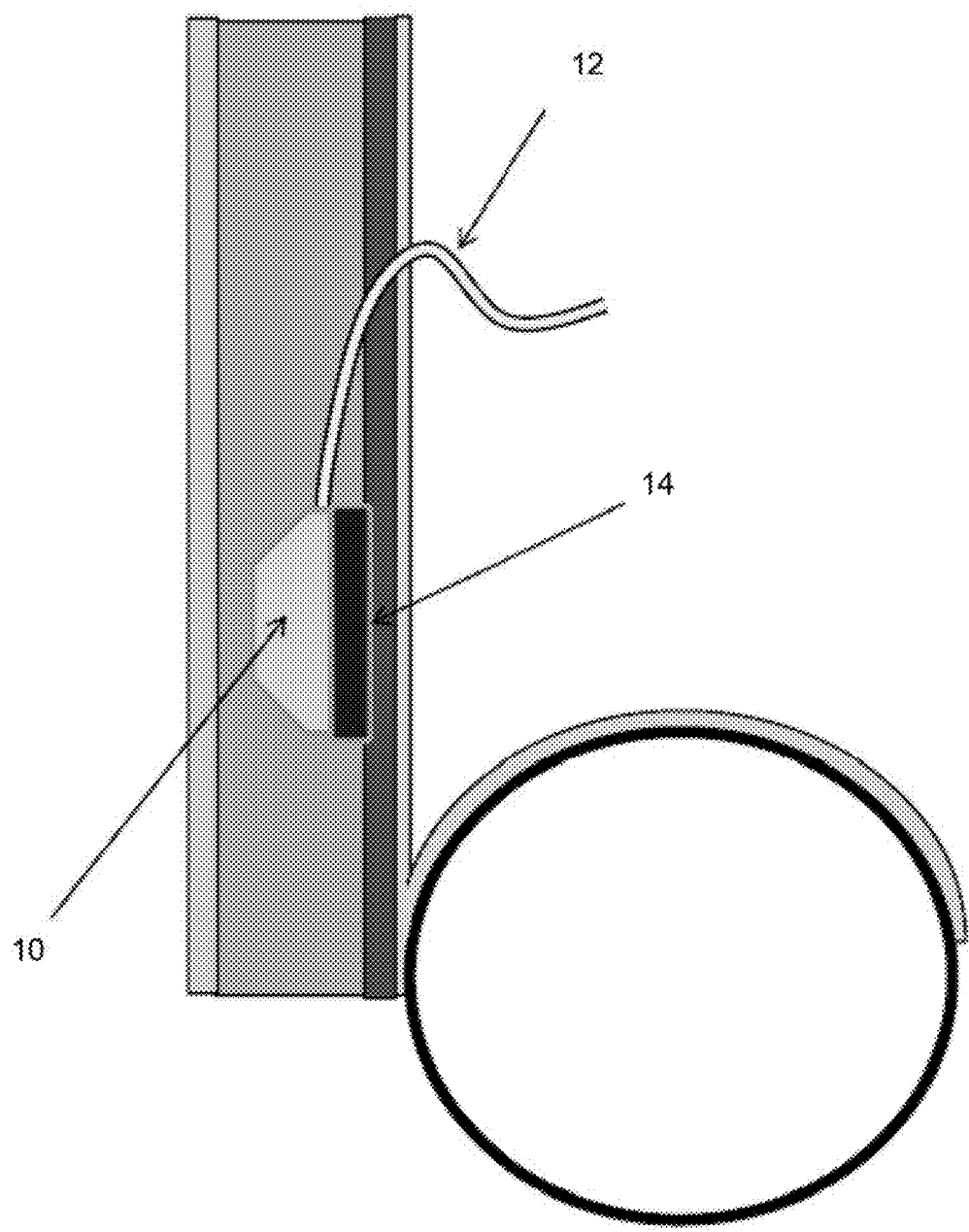
FIG. 1—Side view of the catheter sterilizing element.

FIG. 1—Side view of the catheter sterilizing element 14. In this illustration, a modification to a typical subcutaneous peritoneal port 10 is shown. In this instance, though, the device is shown equipped with an implanted sterilization element 14 (optionally inductively rechargeable) which contains all the circuitry, etc. required to provide effective sterilization of the catheter 12 and/or port 10. In this illustration the sterilization element is shown as manufactured into the device. In addition the sterilization element 14 may also be a device which may be coupled with the implantable device at the time of implantation. In this illustration, as well, an intra peritoneal catheter 12 is shown connected to a subcutaneous port 10, but may include: an IV catheter port, a CNS catheter port, a bladder catheter port, a PICC catheter, a central venous catheter, etc. There may be elements within the catheter 12, as well, to transmit energy, etc., for example, fiberoptics to transmit sterilizing UV or wires to transmit mechanical, ultrasonic or electrical energy. The devices illustrated in this Figure may all be inductively rechargeable.

Figure 2:
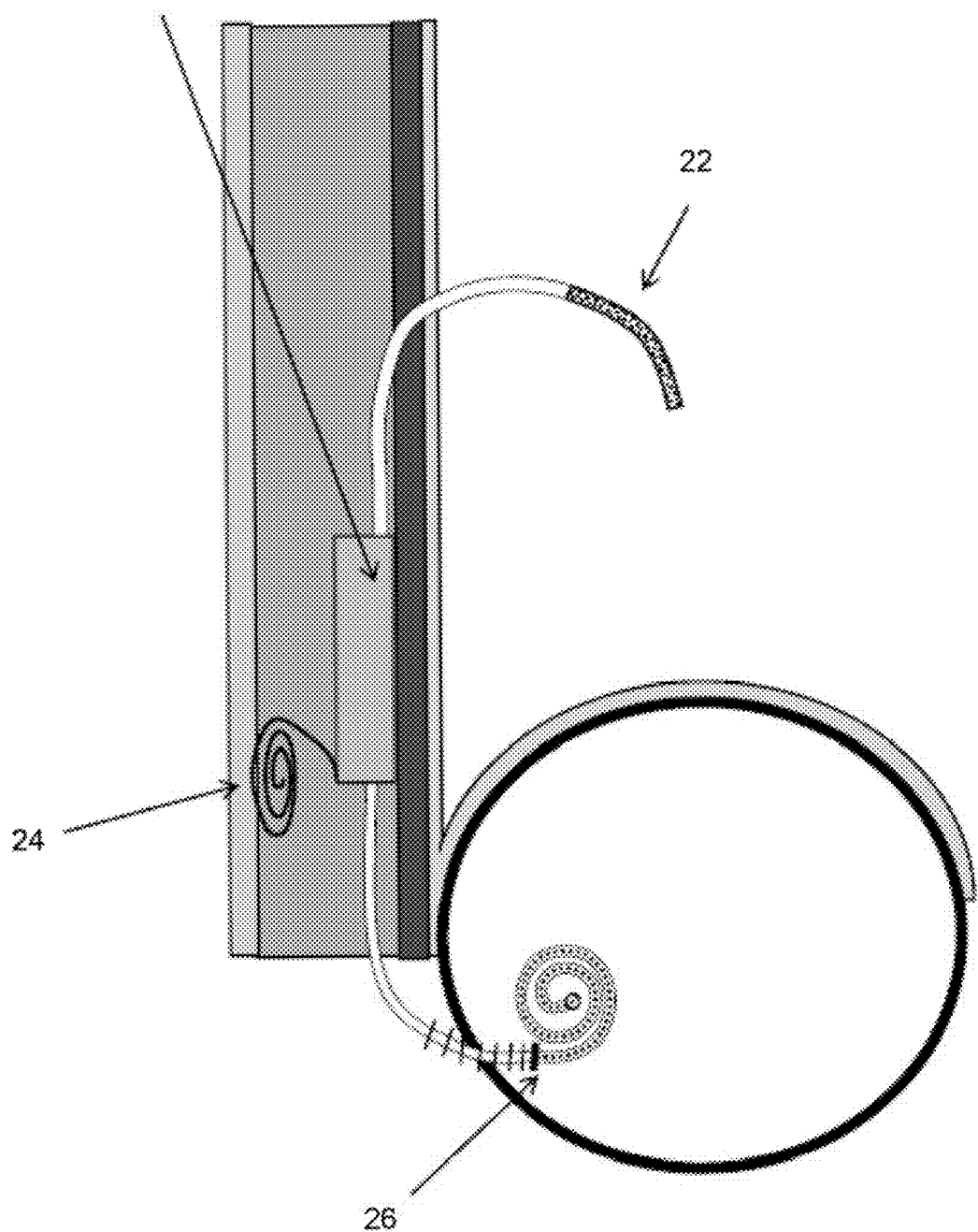
FIG. 2—Side view of the fluid flow sterilization with pump apparatus.

FIG. 2—Side view of the fluid flow sterilization embodiment with pump apparatus. In this illustration, the sterilization element 14 is shown inside of the pump 20 and it may transmit anti-infective to one or both catheters (e.g., ultrasound) or apply anti-infective directly to fluid in the pump 20, e.g., UV sterilization of fluid flow or direct ultrasound to fluid flow or sterilize the surface of the device itself. In this embodiment, as well, the peritoneal catheter 22 may receive active sterilization along with the bladder catheter 26 or on its own or indirectly via the pump 20. The bladder catheter 26 may also receive active sterilization along with the peritoneal catheter 22 or on its own or indirectly via the pump 20. Any of the aforementioned sterilization methods or devices may be used to sterilize the fluid flow and the surface of the device, as well. In this embodiment, the sterilization element 14 may preferably be inductively rechargeable as the implantable pump 20, itself, will likely be rechargeable.

These are but some of the potential embodiments and should not restrict the scope of the invention. The invention described here may be utilized in any implant that requires intermittent or continuous active sterilization to prevent colonization and/or spread of infection from the implant. Other devices for which this technology may be utilized include: pacemakers, Implantable Cardioverter Defibrillators, CNS shunts, bladder catheters, suprapubic catheters, cardiovascular valves, mechanical valves, stents, prosthetic joints (knee, hip, etc), plates, screw or other orthopedic devices, electrical stimulators, neuromodulators or other devices.

What is claimed is:

1. A sterilization system for sterilizing an implanted prosthesis, comprising:
    a housing sized for implantation within a patient body and having an ultrasonic energy generator incorporated into a base of the housing;
    a power generator configured for inductive charging; and
    one or more catheters fluidly coupled to the housing,
    wherein the ultrasonic energy generator is in vibratory communication with the housing when the energy generator is activated transcutaneously such that ultrasonic energy is transmittable towards exposed surfaces of the housing and towards exposed surfaces of the one or more catheters fluidly coupled to the housing, and
    wherein the sterilization system is configured to transmit data relating to status or usage statistics of the system to an external device.

2. The system of claim 1 wherein the one or more catheters comprise an intra-peritoneal catheter.

3. The system of claim 2 further comprising a catheter fluidly coupled to a bladder within the patient body.

4. The system of claim 1 further comprising a subcutaneous port fluidly coupled to the housing.

5. The system of claim 1 further comprising fiberoptics optically coupled to the energy generator.

6. The system of claim 1 further comprising a reservoir having a sterilizing chemical in fluid communication with the housing.

7. The system of claim 1 further comprising a pump coupled to the energy generator.

8. The system of claim 1 further comprising a charging coil for inductively charging the energy generator.

9. The system of claim 1 further comprising a battery electrically coupled to the energy generator.

10. A method of sterilizing an implanted prosthesis, comprising:
    activating an ultrasonic energy generator incorporated into a base of a housing which is implanted within a patient body, wherein the ultrasonic energy generator comprises a power generator configured for inductive charging;
    transcutaneously activating the ultrasonic energy generator;
    transmitting ultrasonic energy from the generator and towards an exposed surfaces of the housing and towards an exposed surfaces of one or more catheters fluidly coupled to the housing;
    transmitting data relating to status or usage statistics of the prosthesis to an external device; and,
    removing a biofilm from the housing via the ultrasonic energy.

11. The method of claim 10 further comprising introducing a sterilizing chemical through the housing via a reservoir in fluid communication with the housing.

12. The method of claim 10 further comprising pumping a fluid through the one or more catheters via a pump in communication with the housing.

13. The method of claim 12 further comprising sterilizing the fluid passing through the one or more catheters via the ultrasonic energy.

* * * * *